United States Patent
Yamamoto (10) Patent No.: US 12,303,332 B2
(45) Date of Patent: *May 20, 2025

(54) ULTRASOUND DIAGNOSTIC SYSTEM AND CONTROL METHOD OF ULTRASOUND DIAGNOSTIC SYSTEM

(71) Applicant: FUJIFILM Corporation, Tokyo (JP)

(72) Inventor: Katsuya Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 151 days.

This patent is subject to a terminal disclaimer.

(21) Appl. No.: 18/155,519

(22) Filed: Jan. 17, 2023

(65) Prior Publication Data

US 2023/0157665 A1    May 25, 2023

Related U.S. Application Data

(63) Continuation of application No. PCT/JP2021/008907, filed on Mar. 8, 2021.

(30) Foreign Application Priority Data

Aug. 26, 2020   (JP) ................................ 2020-142290

(51) Int. Cl.
*A61B 8/00*   (2006.01)
*A61B 8/12*   (2006.01)

(52) U.S. Cl.
CPC .............. *A61B 8/4254* (2013.01); *A61B 8/12* (2013.01); *A61B 8/4427* (2013.01); *A61B 8/463* (2013.01)

(58) Field of Classification Search
CPC ....... A61B 8/4254; A61B 8/12; A61B 8/4427; A61B 8/463; A61B 8/085; A61B 8/4472;
(Continued)

(56) References Cited

U.S. PATENT DOCUMENTS

2003/0167005 A1   9/2003   Sakuma et al.
2004/0019270 A1   1/2004   Takeuchi
(Continued)

FOREIGN PATENT DOCUMENTS

JP   2002-209890 A   7/2002
JP   2003-245280 A   9/2003
(Continued)

OTHER PUBLICATIONS

International Search Report issued in PCT/JP2021/008907; mailed Apr. 20, 2021.
(Continued)

*Primary Examiner* — Alexei Bykhovski
(74) *Attorney, Agent, or Firm* — Studebaker Brackett PLLC (57) ABSTRACT

An ultrasound diagnostic system (1) includes an ultrasound probe (2), a handheld type diagnostic apparatus main body (3), and a server (4), the ultrasound probe (2) includes a position sensor (14) that detects a measurement position of the ultrasound probe (2), the diagnostic apparatus main body (3) includes an image generation unit (22) that generates an ultrasound image and a monitor (24), the server (4) detects an organ of a subject by analyzing the ultrasound image and calculates a score of the measurement position with respect to an optimum position in a case of measuring the detected organ by the ultrasound probe (2), and the score is transmitted from the server (4) to the diagnostic apparatus main body (3) and displayed on the monitor (24).

10 Claims, 8 Drawing Sheets

(58) Field of Classification Search
CPC ....... A61B 8/4477; A61B 8/461; A61B 8/467; A61B 8/468; A61B 8/469; A61B 8/5292; A61B 8/0883; A61B 8/465; A61B 8/488; A61B 8/5207; A61B 8/5223; A61B 8/54; A61B 8/565

See application file for complete search history.

(56) References Cited

U.S. PATENT DOCUMENTS

| | | | |
|---|---|---|---|
| 2011/0246129 A1* | 10/2011 | Ishikawa | G06T 7/74 |
| | | | 702/150 |
| 2013/0131510 A1 | 5/2013 | Toma et al. | |
| 2014/0260632 A1* | 9/2014 | Tateyama | A61B 8/40 |
| | | | 73/632 |
| 2017/0119352 A1* | 5/2017 | Anand | A61B 8/463 |
| 2020/0029941 A1 | 1/2020 | Avendi et al. | |
| 2021/0290203 A1* | 9/2021 | Xie | G01S 7/52053 |
| 2022/0225966 A1* | 7/2022 | Raju | A61B 8/5215 |

FOREIGN PATENT DOCUMENTS

| | | |
|---|---|---|
| JP | 2004-016268 A | 1/2004 |
| JP | 2009-056125 A | 3/2009 |
| JP | 2016-022038 A | 2/2016 |
| JP | 2020-137974 A | 9/2020 |
| WO | 2012/164919 A1 | 12/2012 |
| WO | 2018/194762 A1 | 10/2018 |

OTHER PUBLICATIONS

International Preliminary Report on Patentability and Written Opinion issued in PCT/JP2021/008907; issued Feb. 28, 2023.

An Office Action; "Notice of Reasons for Refusal," mailed by the Japanese Patent Office on Nov. 7, 2023, which corresponds to Japanese Patent Application No. 2022-545288 and is related to U.S. Appl. No. 18/155,519; with English language translation.

* cited by examiner

ULTRASOUND DIAGNOSTIC SYSTEM AND CONTROL METHOD OF ULTRASOUND DIAGNOSTIC SYSTEM

CROSS-REFERENCE TO RELATED APPLICATIONS

This application is a Continuation of PCT International Application No. PCT/JP2021/008907 filed on Mar. 8, 2021, which claims priority under 35 U.S.C. § 119(a) to Japanese Patent Application No. 2020-142290 filed on Aug. 26, 2020. The above applications are hereby expressly incorporated by reference, in its entirety, into the present application.

BACKGROUND OF THE INVENTION

1. Field of the Invention

The present invention relates to an ultrasound diagnostic system including a handheld type diagnostic apparatus main body and a control method of the ultrasound diagnostic system.

2. Description of the Related Art

In the related art, an organ in a subject has been measured by capturing an ultrasound image showing a tomographic plane of the subject using an ultrasound diagnostic apparatus. In capturing the ultrasound image, an ultrasound probe is used to transmit an ultrasonic beam into the subject and to receive an ultrasound echo reflected in the subject. As such an ultrasound probe, an ultrasound probe that transmits an ultrasonic beam into the subject in a state of being disposed on a body surface of the subject and an ultrasound probe, which is a so-called intracavitary probe, that transmits an ultrasonic beam into the subject in a state of being inserted into the subject are known. By moving the ultrasound probe to an appropriate measurement position on the body surface of the subject or in the subject, a measurer acquires an ultrasound image of a target organ in the subject and measures the organ.

As described above, it may be difficult for a measurer having a low skill level to dispose the ultrasound probe at an appropriate measurement position corresponding to the organ in the subject to be observed by the measurer. Therefore, for example, as disclosed in JP2004-16268A, an ultrasound diagnostic apparatus has been developed that supports a measurer in capturing an ultrasound image. In the ultrasound diagnostic apparatus of JP2004-16268A, an ultrasound image captured in advance by a skilled person and positional information of an ultrasound probe at the time when the ultrasound image is captured are displayed to the measurer.

SUMMARY OF THE INVENTION

By the way, a portable ultrasound diagnostic apparatus including a so-called handheld type diagnostic apparatus main body consisting of a thin computer such as a so-called tablet terminal and an ultrasound probe has been developed, and the portable ultrasound diagnostic apparatus may be used to perform measurement of the inside of the subject at a place away from a hospital such as a home nursing site. In a case where the measurement of the inside of the subject is performed at a place away from the hospital, a measurer having a low skill level in the ultrasound diagnostic apparatus may perform the measurement of the inside of the subject. Therefore, for example, it is conceivable to use the technique disclosed in JP2004-16268A, but in general, since a monitor provided in a handheld type diagnostic apparatus main body has a size smaller than that of a monitor provided in a so-called stationary type ultrasound diagnostic apparatus, there were cases that information for supporting the measurer in capturing the ultrasound image cannot be sufficiently displayed, and it is difficult for the measurer to smoothly perform the measurement.

Further, in recent years, there has been an increasing demand for not showing a subject an ultrasound image representing a tomographic plane in the subject. However, even though the technique disclosed in JP2004-16268A is used, it is difficult to support measuring the target organ in the subject without displaying an ultrasonic image representing a tomographic plane in the subject on a monitor.

The present invention has been made to solve such a problem in the related art, and an object thereof is to provide an ultrasound diagnostic system and a control method of the ultrasound diagnostic system with which a measurer can smoothly measure an organ in a subject using a handheld type diagnostic apparatus main body while preventing a captured ultrasound image from being seen by the subject.

An ultrasound diagnostic system according to an aspect of the present invention comprises an ultrasound probe; a handheld type diagnostic apparatus main body connected to the ultrasound probe; and a server connected to the diagnostic apparatus main body, in which the ultrasound probe includes a position sensor that detects a measurement position by the ultrasound probe, the diagnostic apparatus main body includes an image generation unit that generates an ultrasound image of a subject by transmitting and receiving an ultrasonic beam using the ultrasound probe, and a monitor, the server detects an organ of an imaged subject by analyzing the ultrasound image and calculates a score of the measurement position with respect to an optimum position in a case of measuring the detected organ by the ultrasound probe, and the score is transmitted from the server to the diagnostic apparatus main body and displayed on the monitor.

The diagnostic apparatus main body may include a main body-side communication unit that transmits the ultrasound image generated by the image generation unit and the measurement position detected by the position sensor in a case of capturing the ultrasound image to the server, and the server may include a server-side communication unit that transmits the score to the diagnostic apparatus main body.

Further, the ultrasound probe may be an intracavitary probe, and the main body-side communication unit may transmit the ultrasound image and the measurement position to the server in a case where the intracavitary probe is connected to the diagnostic apparatus main body.

The diagnostic apparatus main body may display a schematic diagram of the organ detected by the server on the monitor.

In addition, the diagnostic apparatus main body may display the measurement position detected by the position sensor on the monitor to be superimposed on the schematic diagram.

Here, the schematic diagram may consist of a reconstructed image acquired by pre-scanning the subject.

In addition, the diagnostic apparatus main body may include a mode selection unit that selects either a first mode in which the ultrasound image is displayed on the monitor or a second mode in which the schematic diagram and the score are displayed on the monitor.

The server may create a guide for moving the ultrasound probe from the measurement position to the optimum position, and the created guide may be transmitted from the server to the diagnostic apparatus main body and displayed on the monitor.

In addition, the diagnostic apparatus main body may display the score on the monitor by color coding.

A control method of an ultrasound diagnostic system according to another aspect of the present invention is control method of an ultrasound diagnostic system including an ultrasound probe, a handheld type diagnostic apparatus main body, and a server, the control method comprising: detecting a measurement position by the ultrasound probe; generating an ultrasound image of a subject by transmitting and receiving an ultrasonic beam using the ultrasound probe in the diagnostic apparatus main body; detecting an organ of an imaged subject by analyzing the ultrasound image in the server; calculating a score of the measurement position with respect to an optimum position in a case of measuring the detected organ by the ultrasound probe; and displaying the calculated score on a monitor of the diagnostic apparatus main body.

According to the aspect of the present invention, the ultrasound diagnostic system comprises an ultrasound probe; a handheld type diagnostic apparatus main body connected to the ultrasound probe; and a server connected to the diagnostic apparatus main body, in which the ultrasound probe includes a position sensor that detects a measurement position by the ultrasound probe, the diagnostic apparatus main body includes an image generation unit that generates an ultrasound image of a subject by transmitting and receiving an ultrasonic beam using the ultrasound probe, and a monitor, the server detects an organ of an imaged subject by analyzing the ultrasound image and calculates a score of the measurement position with respect to an optimum position in a case of measuring the detected organ by the ultrasound probe, and the score is transmitted from the server to the diagnostic apparatus main body and displayed on the monitor. Therefore, a measurer can smoothly measure the organ in the subject using the handheld type diagnostic apparatus body while preventing the captured ultrasound image from being seen by the subject.

DESCRIPTION OF THE PREFERRED EMBODIMENTS

Hereinafter, embodiments of the present invention will be described with reference to the accompanying drawings.

The explanation of configuration requirements described below is based on a representative embodiment of the present invention, but the present invention is not limited to such an embodiment.

In addition, in the present specification, numerical ranges represented by using "to" mean ranges including numerical values described before and after "to" as a lower limit value and an upper limit value.

In the present specification, "same" includes an error range generally allowed in the technical field.

First Embodiment

Figure 1:
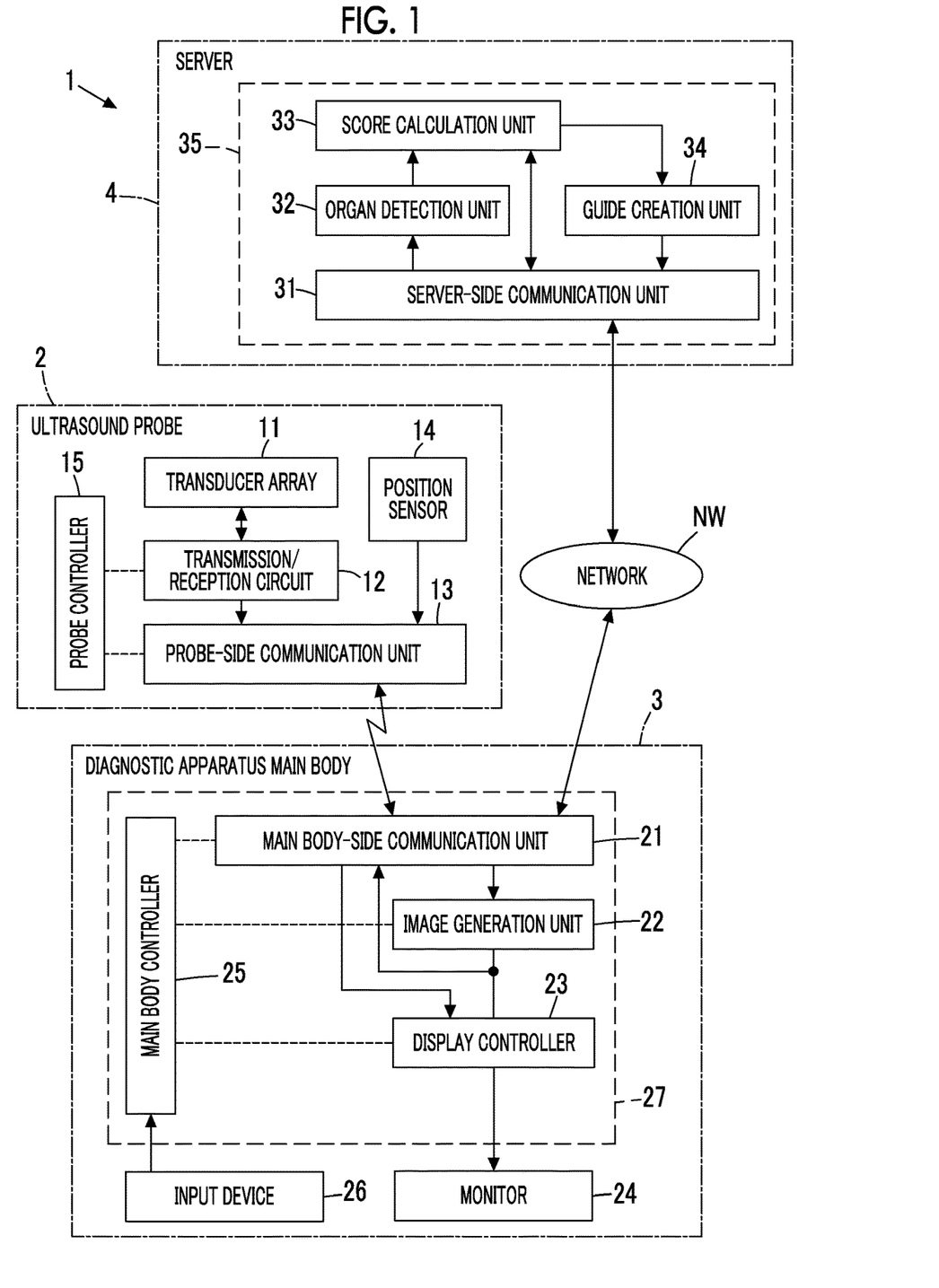
FIG. 1 is a block diagram showing a configuration of an ultrasound diagnostic system according to a first embodiment of the present invention.

FIG. 1 shows a configuration of an ultrasound diagnostic system 1 according to a first embodiment of the present invention. The ultrasound diagnostic system 1 includes an ultrasound probe 2, a diagnostic apparatus main body 3, and a server 4. The ultrasound probe 2 and the diagnostic apparatus main body 3 are connected to each other by wireless communication. The diagnostic apparatus main body 3 and the server 4 are connected to each other via a network NW. The wireless communication or wired communication is used as a connection method between the diagnostic apparatus main body 3 and the network NW and a connection method between the server 4 and the network NW.

The ultrasound probe 2 includes a transducer array 11, and a transmission/reception circuit 12 and a probe-side communication unit 13 are sequentially connected to the transducer array 11. Further, a position sensor 14 is attached to the ultrasound probe 2, and the position sensor 14 is connected to the probe-side communication unit 13. Further, a probe control unit 15 is connected to the transmission/reception circuit 12 and the probe-side communication unit 13.

The diagnostic apparatus main body 3 includes a main body-side communication unit 21, and an image generation unit 22, a display control unit 23, and a monitor 24 are sequentially connected to the main body-side communication unit 21. In addition, the display control unit 23 is connected to the main body-side communication unit 21.

The main body control unit 25 is connected to the main body-side communication unit 21, the image generation unit 22, and the display control unit 23. Further, an input device 26 is connected to the main body control unit 25.

In addition, the main body-side communication unit 21, the image generation unit 22, the display control unit 23, and the main body control unit 25 constitute a main body-side processor 27.

The server 4 includes a server-side communication unit 31, and an organ detection unit 32 and a score calculation unit 33 are sequentially connected to the server-side communication unit 31. Further, the server-side communication unit 31 and a guide creation unit 34 are connected to the score calculation unit 33. The guide creation unit 34 is connected to the server-side communication unit 31.

In addition, the server-side communication unit 31, the organ detection unit 32, the score calculation unit 33, and the guide creation unit 34 constitute a server-side processor 35.

The transducer array 11 of the ultrasound probe 2 shown in FIG. 1 includes a plurality of transducers arranged one-dimensionally or two-dimensionally. Each of the transducers transmits ultrasonic waves in accordance with a drive signal supplied from the transmission/reception circuit 12, receives an ultrasound echo from the subject, and outputs a signal based on the ultrasound echo. Each transducer is constituted by forming electrodes at both ends of a piezoelectric body composed of, for example, a piezoelectric ceramic represented by lead zirconate titanate (PZT), a polymeric piezoelectric element represented by polyvinylidene difluoride (PVDF), and a piezoelectric single crystal represented by lead magnesium niobate-lead titanate (PMN-PT).

Figure 2:
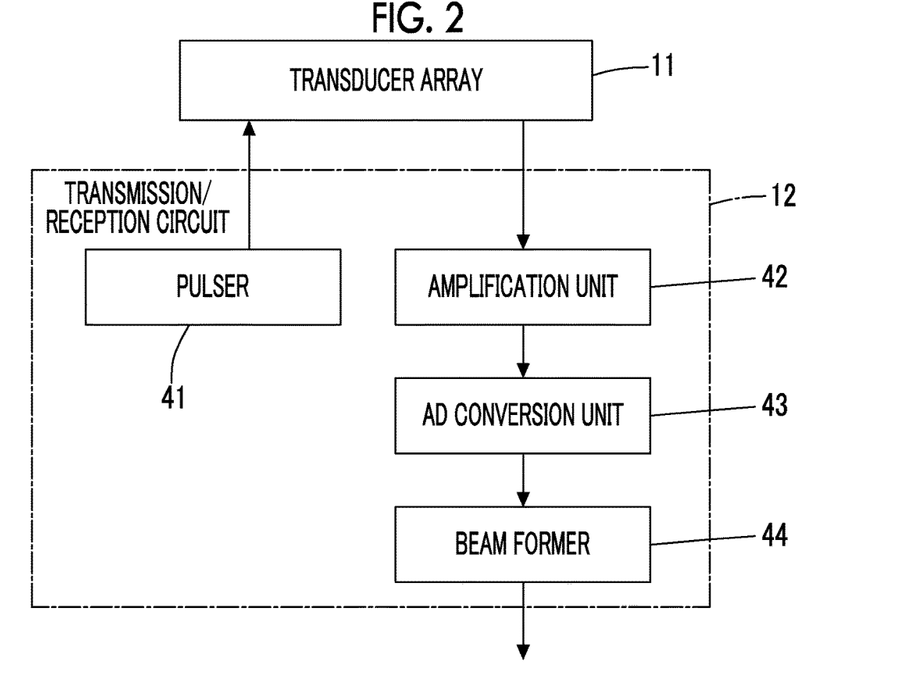
FIG. 2 is a block diagram showing a configuration of a transmission/reception circuit in the first embodiment of the present invention.

Under control of the probe control unit 15, the transmission/reception circuit 12 transmits ultrasonic waves from the transducer array 11 and generates a sound ray signal based on a reception signal acquired by the transducer array 11. As shown in FIG. 2, the transmission/reception circuit 12 includes a pulser 41 connected to the transducer array 11, and an amplification unit 42, and an AD (Analog to Digital) conversion unit 43, and a beam former 44 that are sequentially connected in series from the transducer array 11.

The pulser 41 includes, for example, a plurality of pulse generators, and supplies respective drive signals to a plurality of transducers of the transducer array 11 by adjusting a delay amount such that ultrasonic waves transmitted from the plurality of transducers form an ultrasonic beam based on a transmission delay pattern selected in response to a control signal from the probe control unit 15. In this way, in a case where a pulsed or continuous-wave voltage is applied to the electrodes of the transducers of the transducer array 11, the piezoelectric body expands and contracts, pulsed or continuous-wave ultrasonic waves are generated from the respective transducers, and the ultrasonic beam is formed from a composite wave of the ultrasonic waves.

The transmitted ultrasonic beam is reflected by, for example, a target such as a portion of a subject and propagates toward the transducer array 11 of the ultrasound probe 2. The ultrasound echo propagating toward the transducer array 11 in this way is received by each of the transducers constituting the transducer array 11. At this time, each of the transducers constituting the transducer array 11 expands and contracts by receiving the propagating ultrasound echo to generate reception signals which are electric signals, and outputs the reception signals to the amplification unit 42.

The amplification unit 42 amplifies the signals input from each of the transducers constituting the transducer array 11, and transmits the amplified signals to the AD conversion unit 43. The AD conversion unit 43 converts the signals transmitted from the amplification unit 42 into digital reception data and transmits the reception data to the beam former 44. The beam former 44 performs so-called reception focus processing by adding the respective reception data converted by the AD conversion unit 43 while giving delays thereof according to sound velocities or a distribution of the sound velocities set based on a reception delay pattern selected in response to the control signal from the probe control unit 15. By this reception focus processing, the respective reception data converted by the AD conversion unit 43 are phase-adjusted and added, and a sound ray signal in which the focus of the ultrasound echo is narrowed down is acquired.

The probe-side communication unit 13 includes an antenna for transmitting and receiving radio waves and the like, and performs wireless communication with the main body-side communication unit 21 of the diagnostic apparatus main body 3 under the control of the probe control unit 15. At this time, the probe-side communication unit 13 generates a transmission signal representing the sound ray signal by modulating a carrier based on the sound ray signal generated by the transmission/reception circuit 12 and wirelessly transmits the generated transmission signal to the main body-side communication unit 21 of the diagnostic apparatus main body 3.

As a modulation method of the carrier, for example, amplitude shift keying (ASK), phase shift keying (PSK), quadrature phase shift keying (QPSK), 16 quadrature amplitude modulation (16QAM) and the like are used.

The probe control unit 15 controls each unit of the ultrasound probe 2 based on a program stored in advance.

The position sensor 14 is attached to the ultrasound probe 2 and detects a measurement position of the ultrasound probe 2. The position sensor 14 can include, for example, a magnetic sensor, a gyro sensor, an acceleration sensor, or the like.

Further, although not shown, a battery that supplies power to each unit of the ultrasound probe 2 is built in the ultrasound probe 2.

The diagnostic apparatus main body 3 is a portable so-called handheld type device and is composed of, for example, a thin computer called a tablet type terminal.

The main body-side communication unit 21 of the diagnostic apparatus main body 3 includes an antenna for transmitting and receiving radio waves and the like as in the probe-side communication unit 13, and performs wireless communication with the probe-side communication unit 13 of the ultrasound probe 2 and communication with the server-side communication unit 31 of the server 4 via the network NW under the control of the main body control unit 25. The wireless communication or wired communication is used for connection between the main body-side communication unit 21 and the network NW.

In a case of wireless communication with the probe-side communication unit 13, the main body-side communication unit 21 demodulates the transmission signal wirelessly transmitted from the probe-side communication unit 13 to obtain a sound ray signal. The main body-side communication unit 21 transmits the obtained sound ray signal to the image generation unit 22.

In addition, the main body-side communication unit 21 modulates the carrier based on control information for controlling the ultrasound probe 2, which is input by the measurer via the input device 26, to generate a transmission signal representing a control signal or the like and wirelessly transmits the generated transmission signal to the probe-side communication unit 13. As a modulation method of the carrier, for example, ASK, PSK, QPSK, 16QAM, and the like are used as in the modulation method used by the probe-side communication unit 13.

Figure 3:
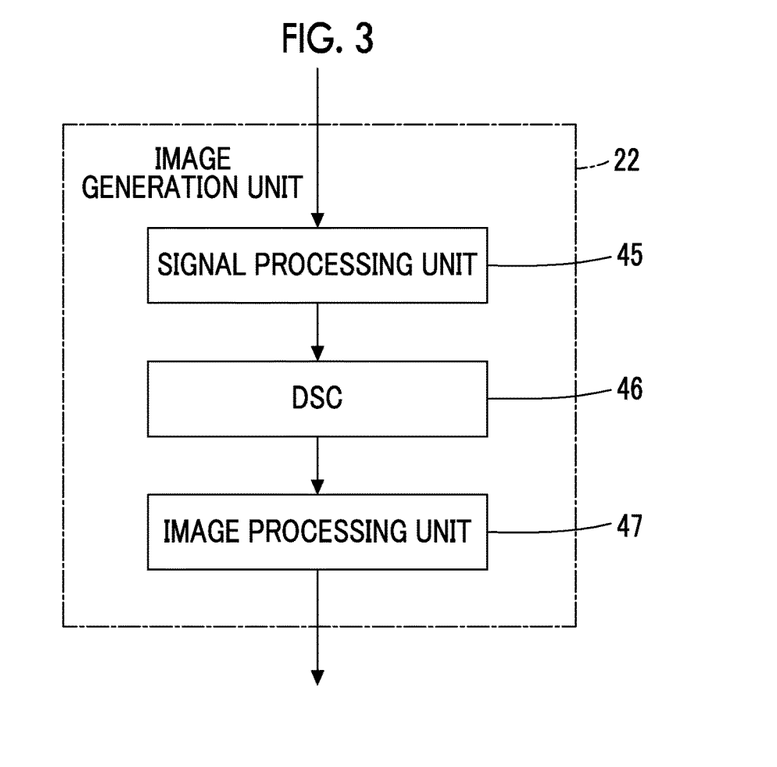
FIG. 3 is a block diagram showing a configuration of an image generation unit in the first embodiment of the present invention.

As shown in FIG. 3, the image generation unit 22 has a configuration in which a signal processing unit 45, a digital scan converter (DSC) 46, and an image processing unit 47 are connected in series.

The signal processing unit 45 generates a B-mode image signal which is tomographic image information about a tissue in the subject by performing correction for attenuation by a distance according to a depth of a reflection position of the ultrasonic wave and then performing envelope detection processing, on the sound ray signal transmitted from the main body-side communication unit 21.

The DSC 46 converts (raster-converts) the B-mode image signal generated by the signal processing unit 45 into an image signal according to a normal television signal scanning method.

The image processing unit 47 performs various types of necessary image processing such as gradation processing on the B-mode image signal input from the DSC 46 and then transmits the B-mode image signal to the main body-side communication unit 21 or the display control unit 23 in response to a command by the main body control unit 25. Hereinafter, the B-mode image signal that has undergone image processing by the image processing unit 47 is simply referred to as an ultrasound image.

Under the control of the main body control unit 25, the display control unit 23 performs predetermined processing on the ultrasound image or the like generated by the image generation unit 22 and displays the ultrasound image or the like on the monitor 24.

The monitor 24 performs various displays under the control of the display control unit 23. The monitor 24 includes, for example, a display device such as a liquid crystal display (LCD) or an organic electroluminescence display.

The input device 26 is used for the measurer to perform an input operation and includes a touch panel disposed to be superimposed on the monitor 24, a button (not shown), a switch (not shown), and the like.

The main body control unit 25 controls each unit of the diagnostic apparatus main body 3 based on a control program stored in advance or the like.

Further, the main body-side processor 27 including the image generation unit 22, the display control unit 23, and the main body control unit 25 is configured of a central processing unit (CPU) and a control program for causing the CPU to perform various types of processing, but may be configured using a field programmable gate array (FPGA), a digital signal processor (DSP), an application specific integrated circuit (ASIC), a graphics processing unit (GPU), or other integrated circuit (IC), or may be configured of a combination thereof.

In addition, the image generation unit 22, the display control unit 23, and the main body control unit 25 of the main body-side processor 27 can also be configured by being partially or wholly integrated into one CPU or the like.

The server-side communication unit 31 of the server 4 includes an antenna for transmitting and receiving radio waves and the like as in the probe-side communication unit 13 and the main body-side communication unit 21 and performs communication with the main body-side communication unit 21 via the network NW. The wireless communication or wired communication is used for connection between the server-side communication unit 31 and the network NW.

The organ detection unit 32 detects the organ of the subject reflected in the ultrasound image by analyzing the ultrasound image generated by the image generation unit 22. As a method of detecting the organ of the subject, the organ detection unit 32 can use, for example, a so-called deep learning method, a so-called template matching method, a machine learning method using support vector machine (SVM), adaboost, and the like, a machine learning method described in Csurka et al.: Visual Categorization with Bags of Keypoints, Proc. of ECCV Workshop on Statistical Learning in Computer Vision, pp. 59-74 (2004), and the like.

The score calculation unit 33 calculates, based on an image of the organ of the subject detected by the organ detection unit 32, a score of the measurement position of the ultrasound probe 2 detected by the position sensor 14 with respect to an optimum position in a case of measuring the organ by the ultrasound probe 2. More specifically, the score is an index indicating a degree of optimality of the measurement position of the ultrasound probe 2 where the ultrasound image including the organ is captured in the measurement of the organ detected by the organ detection unit 32. For example, the score becomes larger as the measurement position of the ultrasound probe 2 where the ultrasound image including the organ detected by the organ detection unit 32 is captured is closer to the optimum position for measuring the organ, and the score becomes smaller as the measurement position is farther from the optimum position.

For example, the score calculation unit 33 can calculate a sharpness of an edge in the image of the organ detected by the organ detection unit 32, estimate an optimum position for measuring the organ based on the calculated sharpness, and compare the estimated optimum position with the measurement position detected by the position sensor 14 to calculate the score. Further, in a case where the organ detected by the organ detection unit 32 is an organ having a bag shape such as the uterus, the score calculation unit 33 can calculate, for example, a circularity of the bag shape of the organ and estimate the optimum position for measuring the organ based on the calculated circularity.

In addition, the score calculation unit 33 can also calculate an evaluation value regarding a position in the ultrasound image of the organ detected by the organ detection unit 32 by analyzing the ultrasound image generated by the image generation unit 22 and received via the main body-side communication unit 21, the network NW, and the server-side communication unit 31 by using, for example, a method disclosed in JP2016-22038A, and estimate the optimum position based on the calculated evaluation value.

Figure 4:
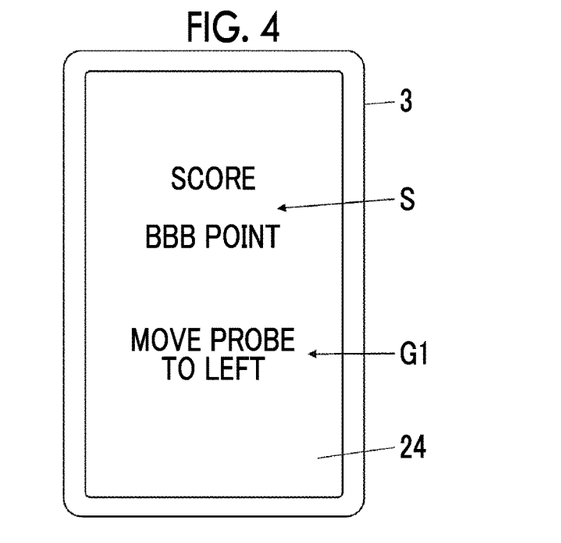
FIG. 4 is a diagram showing an example of a score displayed on a monitor in the first embodiment of the present invention.

The score calculated by the score calculation unit 33 is displayed, for example, on the monitor 24 as shown in FIG. 4, via the server-side communication unit 31, the network NW, the main body-side communication unit 21, the image generation unit 22, and the display control unit 23. In the example of FIG. 4, a numerical value representing the score S is displayed on the monitor 24.

The guide creation unit 34 creates guide information for guiding a measurer to operate the ultrasound probe 2 by using the score S calculated by the score calculation unit 33 and the information about the measurement position of the ultrasound probe 2 detected by the position sensor 14. The guide information created by the guide creation unit 34 is displayed, for example, on the monitor 24 as shown in FIG.

4, as a guide G1, via the server-side communication unit 31, the network NW, the main body-side communication unit 21, the image generation unit 22, and the display control unit 23. In the example of FIG. 4, the text "MOVE PROBE TO LEFT" is displayed on the monitor 24 as the guide G1.

Further, the server-side processor 35 including the server-side communication unit 31, the organ detection unit 32, the score calculation unit 33, and the guide creation unit 34 is configured of a CPU and a control program for causing the CPU to perform various types of processing, but may be configured using a DSP, an ASIC, a GPU, or other ICs, or may be configured of a combination thereof.

In addition, the server-side communication unit 31, the organ detection unit 32, the score calculation unit 33, and the guide creation unit 34 of the server-side processor 35 can also be configured by being partially or wholly integrated into one CPU or the like.

Figure 5:
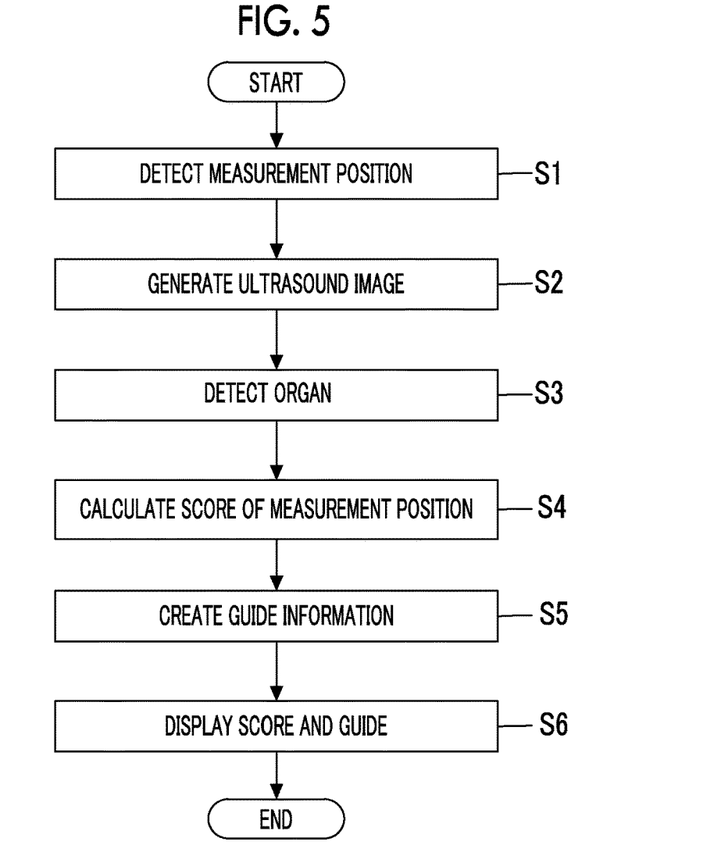
FIG. 5 is a flowchart showing an operation of the ultrasound diagnostic system according to the first embodiment of the present invention.

In the following, a basic operation of the ultrasound diagnostic system 1 according to the first embodiment will be described in detail with reference to the flowchart shown in FIG. 5.

Here, as general types of the ultrasound probe, an ultrasound probe for capturing an ultrasound image in a state of being disposed on the body surface of the subject and an ultrasound probe called an intracavitary probe for capturing an ultrasound image in a state of being inserted into the subject are known. In the following description of the operation, an example in which the ultrasound probe 2 according to the first embodiment of the present invention is an intracavitary probe will be described, but the same operation will be performed in a case of the ultrasound probe for capturing an ultrasound image in a state of being disposed on the body surface of the subject.

First, in step S1, the measurer inserts the ultrasound probe 2 into the subject and moves the ultrasound probe 2 to a measurement position for measuring a target organ. At this time, the position sensor 14 attached to the ultrasound probe 2 detects the measurement position of the ultrasound probe 2.

Next, in step S2, an ultrasound image is captured in a state in which the ultrasound probe 2 is arranged at the measurement position where the measurement position was detected in step S1. At this time, the ultrasonic beams are transmitted from the plurality of transducers of the transducer array 11 into the subject in accordance with the drive signal from the pulser 41 of the transmission/reception circuit 12, and the reception signal is output to the amplification unit 42 of the transmission/reception circuit 12 from each transducer that has received the ultrasound echo from the subject. The reception signals are amplified by the amplification unit 42, subjected to AD conversion by the AD conversion unit 43, and then phase-adjusted and added by the beam former 44 to generate the sound ray signal. The sound ray signal is wirelessly transmitted from the probe-side communication unit 13 to the main body-side communication unit 21 and transmitted to the image generation unit 22. The image generation unit 22 performs various types of processing on the sound ray signal to generate the ultrasound image.

The ultrasound image generated in this way is transmitted to the organ detection unit 32 via the main body-side communication unit 21, the network NW, and the server-side communication unit 31.

In step S3, the organ detection unit 32 detects the organ of the subject included in the ultrasound image by analyzing the ultrasound image generated in step S2. At this time, the organ detection unit 32 can detect the organ by using, for example, a deep learning method, a template matching method, or a machine learning method using SVM, adaboost, or the like.

In step S4, the score calculation unit 33 calculates, based on an image of the organ of the subject detected in step S3, a score S of the measurement position of the ultrasound probe 2 detected in step S1 with respect to an optimum position in a case of measuring the organ by the ultrasound probe 2. For example, the score calculation unit 33 can calculate a sharpness of an edge in the image of the organ detected by the organ detection unit 32, estimate an optimum position for measuring the organ based on the calculated sharpness, and compare the estimated optimum position with the measurement position detected in step S1 to calculate the score S.

The score calculated in this way is transmitted to the guide creation unit 34 and transmitted to the monitor 24 via the server-side communication unit 31, the network NW, the main body-side communication unit 21, the image generation unit 22, and the display control unit 23.

In step S5, the guide creation unit 34 creates guide information for guiding the measurer to operate the ultrasound probe 2 by using information indicating the measurement position of the ultrasound probe 2 detected in step S1 and the score S calculated in step S4. For example, the guide creation unit 34 can create guide information for guiding the measurer on a direction in which the ultrasound probe 2 should be moved in order to more clearly depict the organ detected in step S3 in the ultrasound image.

The guide information created in this way is transmitted to the monitor 24 via the server-side communication unit 31, the network NW, the main body-side communication unit 21, the image generation unit 22, and the display control unit 23.

Finally, in step S6, the score S and the guide G1 are displayed on the monitor 24, for example, as shown in FIG. 4. By moving the ultrasound probe 2 while checking the score S and the guide G1 displayed in this way, the measurer can dispose the ultrasound probe 2 at an optimum measurement position for measuring the target organ and capture the ultrasound image.

Here, in general, there is a case where the measurement of the inside of the subject is performed at a place away from a hospital, such as in a home nursing site, by using the ultrasound diagnostic apparatus including the handheld type diagnostic apparatus main body and the ultrasound probe. As described above, in a case where the measurement of the inside of the subject is performed at a place away from the hospital, the measurement of the subject may not be smoothly performed because the measurer having a low skill level in the ultrasound diagnostic apparatus performs the measurement of the inside of the subject.

Further, in recent years, there has been an increasing demand for not showing a subject an ultrasound image representing a tomographic plane in the subject. In the ultrasound diagnostic apparatus in the related art, the measurer needs to dispose the ultrasound probe at the optimum measurement position for measuring a target site while checking the ultrasound image currently being captured and at that time, the ultrasound image may be seen by the subject.

According to the ultrasound diagnostic system 1 according to the first embodiment of the present invention, the score S of the measurement position of the ultrasound probe 2 with respect to the optimum position in a case of measuring the target organ by the ultrasound probe 2 can be calculated, the calculated score S is displayed on the monitor 24, and the generated ultrasound image is not displayed on the monitor 24, so that even a measurer having a low skill level can smoothly measure the target organ in the subject by using the handheld type diagnostic apparatus main body while preventing the captured ultrasound image from being seen by the subject.

In addition, as the ultrasound probe 2, instead of the intracavitary probe, an ultrasound probe for capturing the ultrasound image in a state of being disposed on the body surface of the subject can also be used. Even in this case, even a measurer having a low skill level can measure the target organ in the subject by using the handheld type diagnostic apparatus main body while preventing the captured ultrasound image from being seen by the subject. However, in a case where the intracavitary probe is used as the ultrasound probe 2, it is difficult for the measurer to directly check the front end part of the ultrasound probe 2 because the ultrasound probe 2 is inserted into the subject. Therefore, the present invention is more useful.

Therefore, for example, in a case where the main body control unit 25 determines that the intracavitary probe is used as the ultrasound probe 2, the information about the measurement position of the ultrasound probe 2 detected in step S1 and the ultrasound image generated in step S2 can be transmitted to the server 4. For example, as shown in FIG. 6, the main body control unit 25 can also display the buttons B1, B2, and B3 for selecting the type of the ultrasound probe 2 on the monitor 24 and send commands to the main body-side communication unit 21 such that the information about the measurement position detected in step S1 and the ultrasound image generated in step S2 are transmitted to the server 4 in a case where the button B3 corresponding to the intracavitary probe is selected by the measurer via the input device 26.

Figure 6:
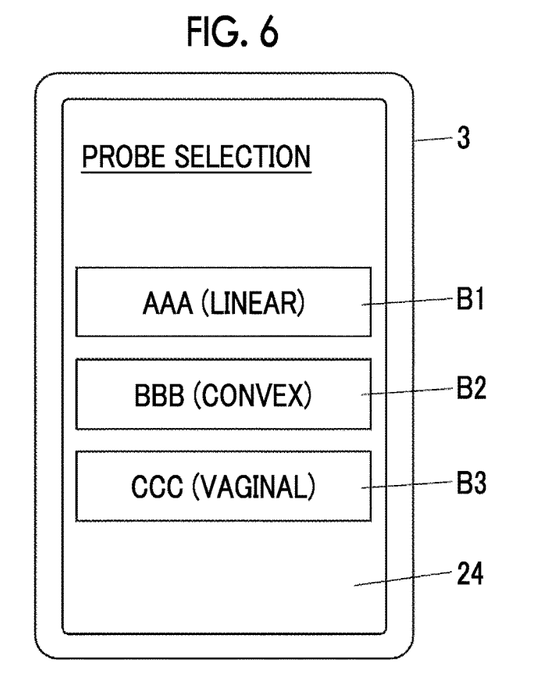
FIG. 6 is a diagram showing an example of a probe selection button for a measurer to select a type of an ultrasound probe in the first embodiment of the present invention.

In the example of FIG. 6, a button B1 for selecting the "AAA (linear)" ultrasound probe, a button B2 for selecting the "BBB (convex)" ultrasound probe, and a button B3 for selecting the "CCC (vaginal)" ultrasound probe are displayed on the monitor 24. "AAA", "BBB", and "CCC" are identifiers of the ultrasound probe 2 such as a model number and a name of the ultrasound probe 2.

In addition, in a case where the main body control unit 25 determines that a preset for an examination using the intracavitary probe is selected, the main body control unit 25 can also send commands to the main body-side communication unit 21 such that the information about the measurement position detected in step S1 and the ultrasound image generated in step S2 are transmitted to the server 4. Here, the preset is a set of preset conditions including imaging conditions such as a gain in a case of generating the ultrasound image and image display conditions such as a contrast in a case of displaying the ultrasound image, according to the type of examination such as an abdominal examination, a gynecological examination and an obstetric examination.

Figure 7:
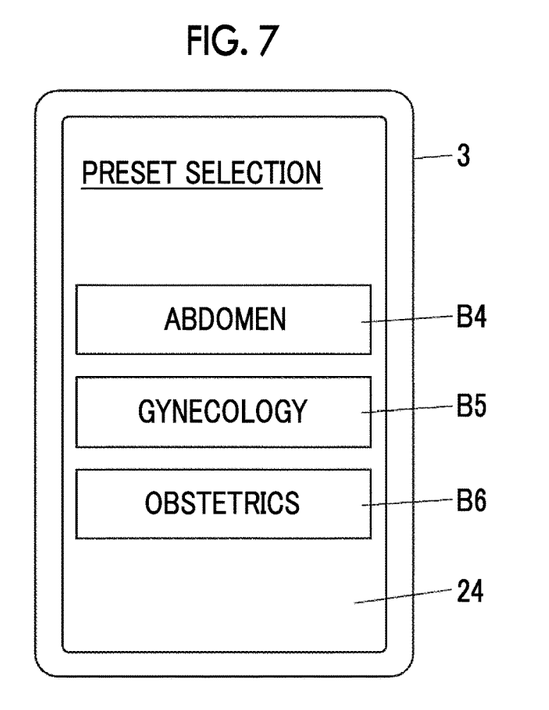
FIG. 7 is a diagram showing an example of a preset selection button for a measurer to select a measurement preset in the first embodiment of the present invention.

For example, as shown in FIG. 7, the main body control unit 25 can also display a button B4 for selecting a preset for the abdomen, a button B5 for selecting a preset for the gynecology, and a button B6 for selecting a preset for the obstetrics on the monitor 24 and send commands to the main body-side communication unit 21 such that the information about the measurement position detected in step S1 and the ultrasound image generated in step S2 are transmitted to the server 4 in a case where the button B5 for selecting a preset for the gynecology that uses the intracavitary probe is selected by the measurer via the input device 26.

In addition, although an example in which the score S is displayed on the monitor 24 as a numerical value is described in step S6, the display method of the score S is not particularly limited to this.

Figure 8:
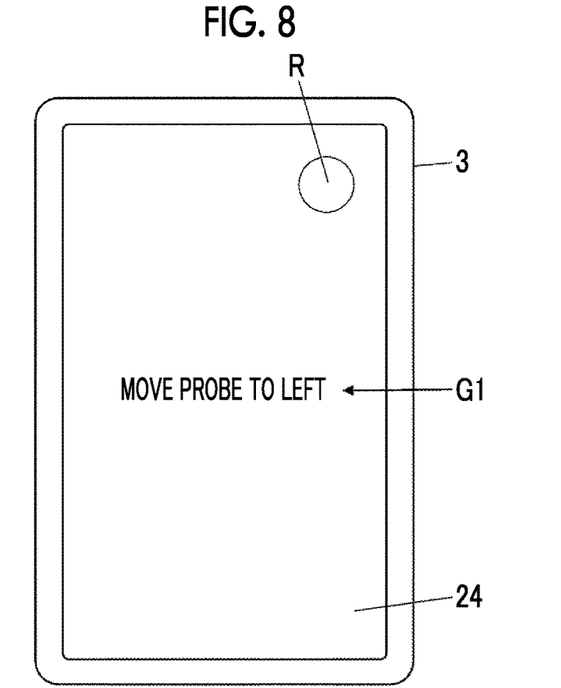
FIG. 8 is a diagram showing an example of a score mark representing a score by color coding in the first embodiment of the present invention.

For example, as shown in FIG. 8, the main body control unit 25 can display the score mark R for indicating the score S in color on the monitor 24 and change a display color of S in color on the monitor 24 by color coding. For example, the main body control unit 25 can display the score mark R in red in a case where the score S is smaller than a first value, displays the score mark R in yellow in a case where the score S is equal to or greater than the first value and is smaller than a second value, and display the score mark R in blue in a case where the score S is equal to or greater than the second value.

In addition, the main body control unit 25 can also change a display color of an entirety of the monitor 24, that is, the background, according to a value of the score S.

Figure 9:
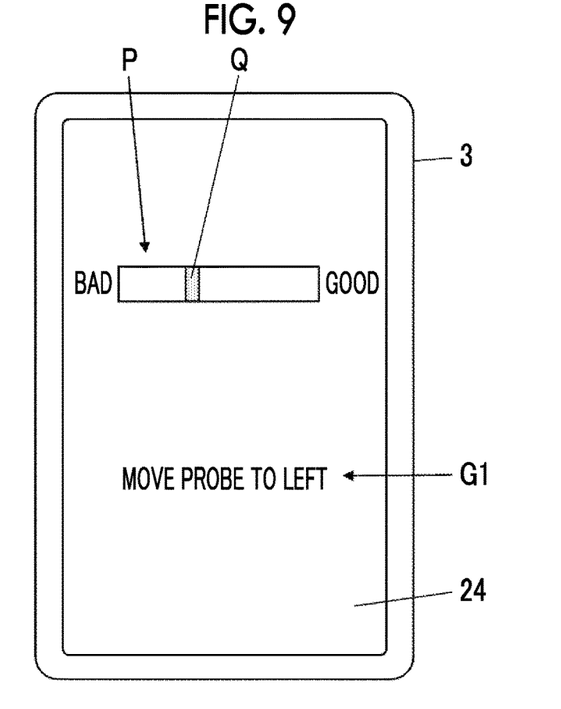
FIG. 9 is a diagram showing an example of a meter representing the score in the first embodiment of the present invention.

In addition, the main body control unit 25 can also represent the score S by the meter P, for example, as shown in FIG. 9. In the example of FIG. 9, the meter P includes a needle portion Q and indicates that the score S is lower as the needle portion Q is disposed at a position closer to the left "BAD", and the score S is higher as the needle portion Q is disposed at a position closer to the right "GOOD".

Further, although the guide information is created in step S5 and the guide G1 is displayed on the monitor 24 in step S6, only the score S out of the score S and the guide G1 may be displayed on the monitor 24. Even in this case, the measurer can dispose the ultrasound probe 2 at the optimum measurement position for measuring the target site by moving the ultrasound probe 2 while checking the score S displayed on the monitor 24.

Second Embodiment

In the first embodiment, an example is shown in which a numerical value representing the score S and the guide G1 consisting of the text are displayed on the monitor 24. However, in order to prevent the ultrasound image from being seen by the subject and to allow the measurer to perform the measurement more smoothly, the schematic diagram of the organ currently being measured may be displayed on the monitor 24.

Figure 10:
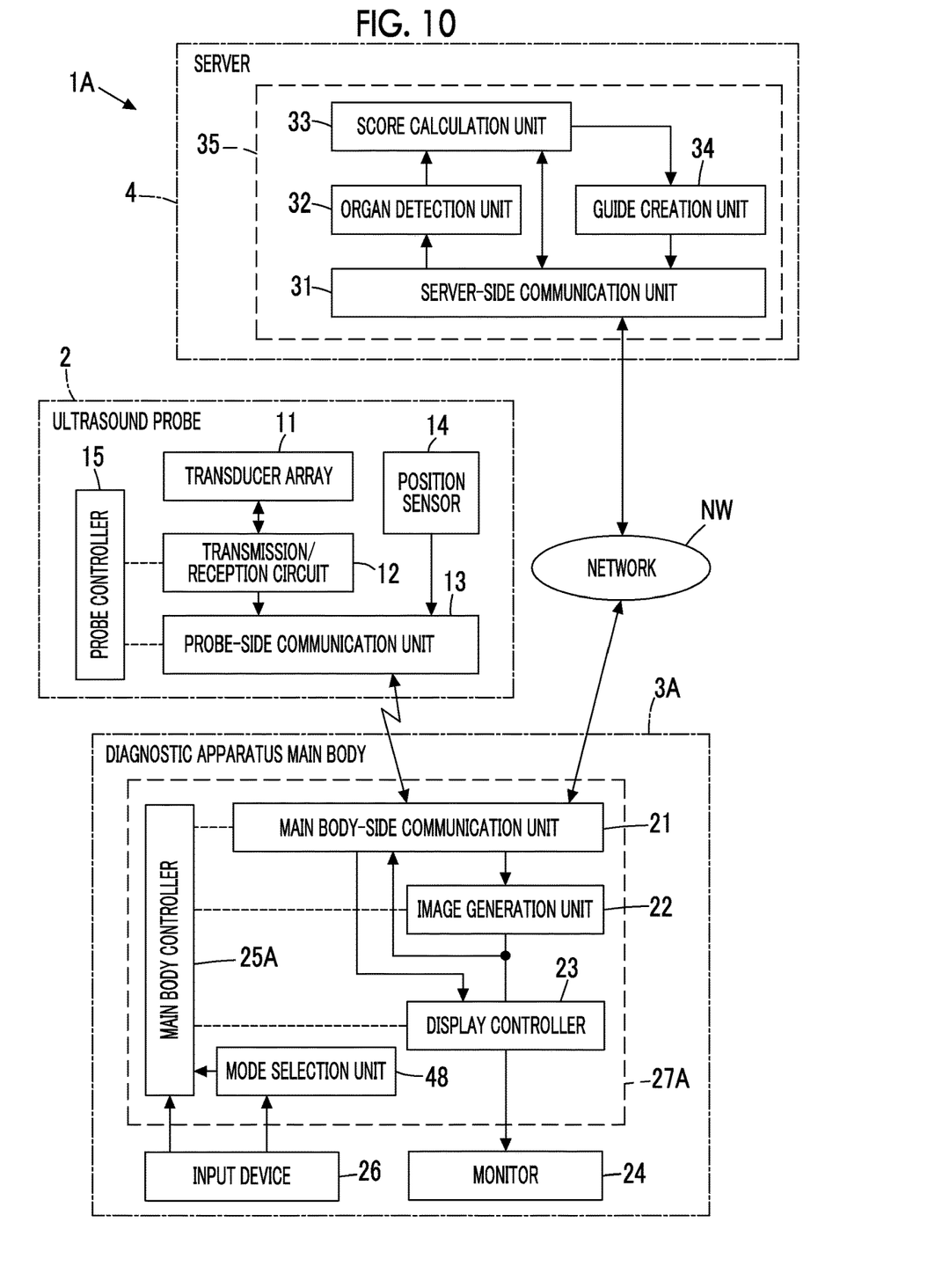
FIG. 10 is a diagram showing a configuration of an ultrasound diagnostic system according to a second embodiment of the present invention.

FIG. 10 shows a configuration of an ultrasound diagnostic system 1A according to the second embodiment. The ultrasound diagnostic system 1A includes a diagnostic apparatus main body 3A instead of the diagnostic apparatus main body 3 in the ultrasound diagnostic system 1 of the first embodiment shown in FIG. 1.

In the diagnostic apparatus main body 3A, a mode selection unit 48 is added and a main body control unit 25A is provided in place of the main body control unit 25 in the diagnostic apparatus main body 3A according to the first embodiment. The mode selection unit 48 is connected to the main body control unit 25A and the input device 26. Further, a main body-side processor 27A including the mode selection unit 48 is configured instead of the main body-side processor 27.

Figure 11:
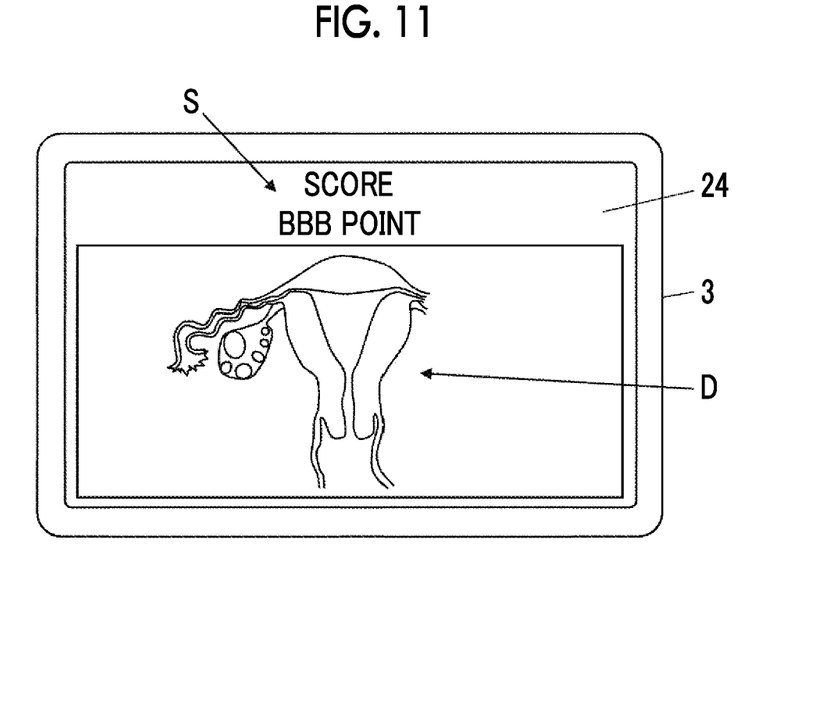
FIG. 11 is a diagram showing an example of a schematic diagram of an organ displayed on the monitor in the second embodiment of the present invention.

The main body control unit 25 stores schematic diagrams of a plurality of organs, selects a schematic diagram of the organ detected by the organ detection unit 32 of the server 4, and displays the schematic diagram D on the monitor 24 as shown in FIG. 11. In FIG. 11, the schematic diagram D of the uterus of the subject is displayed on the monitor 24 together with the score S.

By checking the schematic diagram D displayed on the monitor 24, the measurer can easily understand which organ the ultrasound image is currently being captured.

Figure 12:
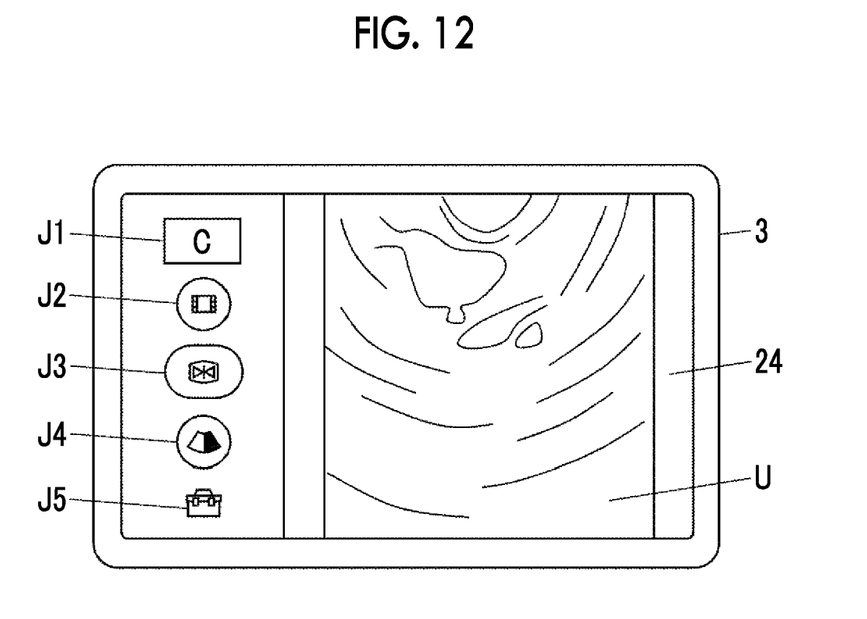
FIG. 12 is a diagram schematically showing an example of a first mode in which an ultrasound image is displayed on the monitor in the second embodiment of the present invention.

In addition, the mode selection unit 48 selects either a first mode in which the ultrasound image U is displayed on the monitor 24 as shown in FIG. 12 or a second mode in which the schematic diagram D of the organ and the score S are displayed as shown in FIG. 11, based on the input operation of the measurer via the input device 26. For example, the mode selection unit 48 can select the first mode in a case where there is a low possibility that the ultrasound image U is seen by the subject and it is desired to check the ultrasound image U and can select the second mode in a case where there is a high possibility that the ultrasound image U is seen by the subject, based on the input operation of the measurer.

In addition, in the first mode, in addition to the ultrasound image U, operation icons J1 to J5 for performing an operation of the ultrasound diagnostic system 1A can be displayed on the monitor 24. For example, the operation icon J1 is used for switching an examination mode, the operation icon J2 is used for storing the ultrasound images U of a plurality of frames continuously generated within a fixed time period, the operation icon J3 is used for freeze-displaying the ultrasound image U on the monitor 24, the operation icon J4 is used for changing so-called gain and depth, and operation icon J5 is used for displaying a plurality of other operation icons (not shown) on the monitor 24.

As described above, according to the ultrasound diagnostic system 1A of the second embodiment of the present invention, the measurer can easily understand the organ currently being measured by checking the schematic diagram D of the organ displayed on the monitor 24. Therefore, the measurer can more smoothly measure the organ of the subject.

In addition, since the first mode in which the ultrasound image U is displayed and the second mode in which the schematic diagram D of the organ and the score S are displayed are switched by the input operation of the measurer via the input device 26, it is possible for the measurer to check the ultrasound image U while preventing the ultrasound image U from being seen by the subject, and thus the measurer can more smoothly measure the organ of the subject.

Further, it has been described that the main body control unit 25A stores the schematic diagrams D of a plurality of organs. However, for example, the server 4 can be provided with a memory (not shown) storing the schematic diagrams D of the plurality of organs and the schematic diagram D of the organ detected by the organ detection unit 32 can be displayed on the monitor 24 by a command from the main body control unit 25A via the server-side communication unit 31, the network NW, the main body-side communication unit 21, the image generation unit 22, and the display control unit 23.

In addition, the reconstructed image acquired by pre-scanning the subject may be used as the schematic diagram D of the organ. The pre-scanning is scanning performed to roughly check the status inside the subject using the ultrasound probe 2 used for the measurement before the measurement of the organ of the subject is performed. For example, the main body control unit 25A can generate the reconstructed image by generating three-dimensional voxel data of the target organ based on the captured ultrasound images U of a plurality of frames by using the technique disclosed in JP2002-209890A.

Further, for example, instead of generating the reconstructed image by the diagnostic apparatus main body 3A, the server 4 may be provided with a reconstructed image generation unit for generating the reconstructed image, and the reconstructed image generation unit of the server 4 may generate the reconstructed image.

In addition, the measurement position of the ultrasound probe 2 detected by the position sensor 14 can also be displayed on the monitor 24 by being superimposed on the schematic diagram D of the organ.

Figure 13:
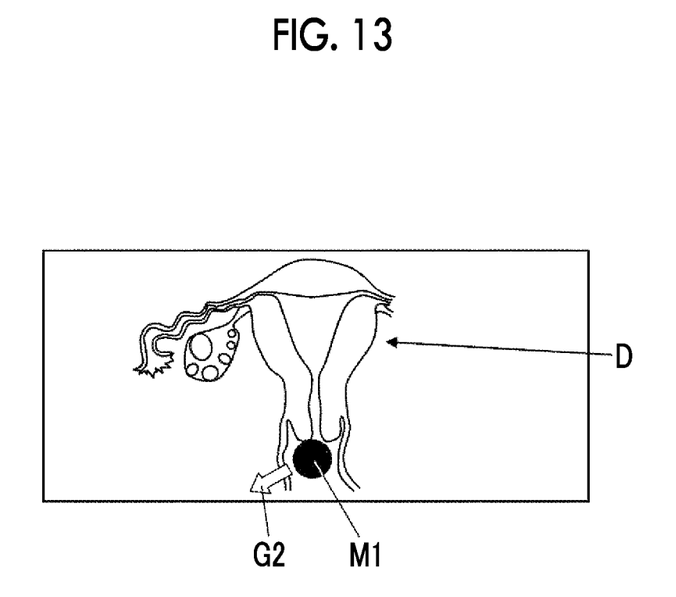
FIG. 13 is a diagram showing an example of a probe mark displayed on the monitor in the second embodiment of the present invention.

For example, as shown in FIG. 13, the main body control unit 25A can superimpose the probe mark M1 indicating the position of the front end part of the ultrasound probe 2 on the schematic diagram D of the organ. As a result, the measurer can easily understand the position of the ultrasound probe 2 with respect to the target organ.

Further, at this time, the guide creation unit 34 can indicate a direction in which the ultrasound probe 2 should be moved in order to accurately measure the target organ by an arrow G2. By checking the arrow G2, the measurer can easily move the ultrasound probe 2 to the optimum measurement position for measuring the target organ.

Figure 14:
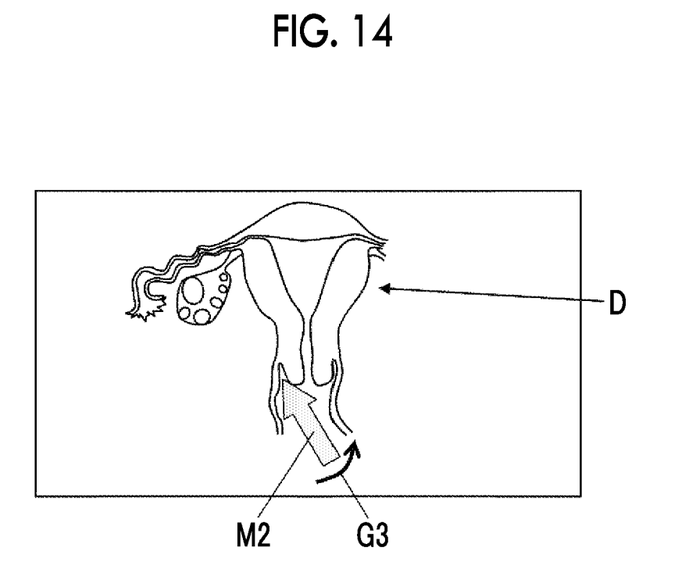
FIG. 14 is a diagram showing another example of a probe mark displayed on the monitor in the second embodiment of the present invention.

In addition, for example, the main body control unit 25A can calculate an orientation of the ultrasound probe 2 with respect to the organ based on the image of the organ detected by the organ detection unit 32 and the measurement position of the ultrasound probe 2 detected by the position sensor 14 and superimpose an arrow-shaped probe mark M2 representing both the calculated orientation of the ultrasound probe 2 and the measurement position thereof on the schematic diagram D of the organ as shown in FIG. 14. As a result, the measurer can easily understand the position and orientation of the ultrasound probe 2 with respect to the target organ.

In addition, for example, by attaching the magnetic sensor to each of the front end part and a rear end part of the ultrasound probe 2, the main body control unit 25A can also calculate a direction from a position of the rear end part of the ultrasound probe 2 toward a position of the front end part of the ultrasound probe 2 as the orientation of the ultrasound probe 2.

In addition, in a case where the position sensor 14 includes a gyro sensor, the orientation of the ultrasound probe 2 can be detected by using the gyro sensor.

In this way, in a case where the arrow-shaped probe mark M2 is superimposed on the schematic diagram D of the organ, the guide creation unit 34 can indicate a rotation direction in which the ultrasound probe 2 should be rotated in order to accurately measure the target organ by an arrow G3. By checking the arrow G3, the measurer can easily rotate the ultrasound probe 2 at an optimum angle for measuring the target organ.

EXPLANATION OF REFERENCES 1, 1A: ultrasound diagnostic system
2: ultrasound probe
3, 3A: diagnostic apparatus main body
4: server
11: transducer array
12: transmission/reception circuit
13: probe-side communication unit
14: position sensor
15: probe control unit
21: main body-side communication unit
22: image generation unit
23: display control unit
24: monitor 25, 25A: main body control unit
26: input device
27: main body-side processor
31: server-side communication unit
32: organ detection unit
33: score calculation unit
34: guide creation unit
35: server-side processor
41: pulser
42: amplification unit
43: AD conversion unit
44: beam former
45: signal processing unit
46: DSC
47: image processing unit
48: mode selection unit
B1 to B6: button
D: schematic diagram
G1: guide
G2, G3: arrow
J1 to J5: operation icon
M1, M2: probe mark
NW: network
P: meter
Q: needle portion
R: score mark
S: score
U: ultrasound image.

What is claimed is:

1. An ultrasound diagnostic system comprising:
an ultrasound probe;
a handheld type diagnostic apparatus main body connected to the ultrasound probe; and
a server connected to the diagnostic apparatus main body,
wherein the ultrasound probe includes
a position sensor configured to detect a measurement position by the ultrasound probe,
the diagnostic apparatus main body includes
a main body processor configured to generate an ultrasound image of a subject by transmitting and receiving an ultrasonic beam using the ultrasound probe, and
a monitor,
the server includes
a server processor configured to
store schematic diagrams of a plurality of organs,
detect an organ of the subject by analyzing the ultrasound image,
select a schematic diagram corresponding to the detected organ from the plurality of schematic diagrams,
calculate a score of the measurement position with respect to an optimum position in measuring the detected organ by the ultrasound probe, and
transmit the score from the server to the diagnostic apparatus main body,
the main body processor is further configured to display the score and the schematic diagram on the monitor.

2. The ultrasound diagnostic system according to claim 1, wherein the main body processor is further configured to transmit the ultrasound image and the measurement position detected by the position sensor in capturing the ultrasound image to the server, and
the server processor is further configured to transmit the score to the diagnostic apparatus main body.

3. The ultrasound diagnostic system according to claim 2, wherein the ultrasound probe is an intracavitary probe, and
the main body processor is further configured to transmit the ultrasound image and the measurement position to the server once the intracavitary probe is connected to the diagnostic apparatus main body.

4. The ultrasound diagnostic system according to claim 1, wherein the schematic diagram consists of a reconstructed image acquired by pre-scanning the subject.

5. The ultrasound diagnostic system according to claim 1, wherein the main body processor is further configured to select either a first mode in which the ultrasound image is displayed on the monitor or a second mode in which the schematic diagram and the score are displayed on the monitor.

6. The ultrasound diagnostic system according to claim 1, wherein the server processor is further configured to
create a guide for moving the ultrasound probe from the measurement position to the optimum position, and
transmit the guide from the server to the diagnostic apparatus main body, and
the main body processor is further configured to display the guide on the monitor.

7. The ultrasound diagnostic system according to claim 2, wherein the server processor is further configured to
create a guide for moving the ultrasound probe from the measurement position to the optimum position, and
transmit the guide from the server to the diagnostic apparatus main body, and
the main body processor is further configured to display the guide on the monitor.

8. The ultrasound diagnostic system according to claim 1, wherein the main body processor is further configured to display the score on the monitor by color coding.

9. A control method of an ultrasound diagnostic system including an ultrasound probe, a handheld type diagnostic apparatus main body, and a server, the control method comprising:
detecting a measurement position by the ultrasound probe;
generating an ultrasound image of a subject by transmitting and receiving an ultrasonic beam using the ultrasound probe in the diagnostic apparatus main body;
storing schematic diagrams of a plurality of organs;
detecting an organ of the subject by analyzing the ultrasound image in the server;
calculating a score of the measurement position with respect to an optimum position in a case of measuring the detected organ by the ultrasound probe in the server;
selecting a schematic diagram corresponding to the detected organ from the plurality of schematic diagrams; and
displaying the calculated score and the schematic diagram on a monitor of the diagnostic apparatus main body.

10. An ultrasound diagnostic system comprising:
an ultrasound probe;
a handheld type diagnostic apparatus main body connected to the ultrasound probe; and
a server connected to the diagnostic apparatus main body,
wherein the ultrasound probe includes
a position sensor configured to detect a measurement position by the ultrasound probe, the diagnostic apparatus main body includes
a main body processor configured to
store schematic diagrams of a plurality of organs, and
generate an ultrasound image of a subject by transmitting and receiving an ultrasonic beam using the ultrasound probe, and
a monitor,
the server includes
a server processor configured to
detect an organ of the subject by analyzing the ultrasound image,
calculate a score of the measurement position with respect to an optimum position in measuring the detected organ by the ultrasound probe, and
transmit the score from the server to the diagnostic apparatus main body,
the main body processor is further configured to
select a schematic diagram corresponding to the detected organ from the plurality of schematic diagrams, and
display the score and the schematic diagram on the monitor.

* * * * *